United States Patent [19]
Hartley et al.

[11] Patent Number: 6,049,735
[45] Date of Patent: Apr. 11, 2000

[54] CARDIAC RHYTHM MANAGEMENT DEVICE WITH DETECTION AND THERAPY FOR SUDDEN SYNCOPAL EVENTS

[75] Inventors: Jesse W. Hartley, Lino Lakes; Wyatt Stahl, Vadnais Heights; John Voegele, East Bethel, all of Minn.

[73] Assignee: Cardiac Pacemakers Inc., St. Paul, Minn.

[21] Appl. No.: 09/259,349

[22] Filed: Mar. 1, 1999

[51] Int. Cl.$^7$ ...................................................... A61N 1/36
[52] U.S. Cl. .................................................................. 607/9
[58] Field of Search ........................................... 607/9, 23

[56] References Cited

U.S. PATENT DOCUMENTS

| 5,284,491 | 2/1994 | Sutton et al. . |
| 5,501,701 | 3/1996 | Markowitz et al. . |
| 5,676,686 | 10/1997 | Jensen et al. . |

OTHER PUBLICATIONS

D.A. Richardson, et al. "Prevalence of Cardioinhibitory Carotid Sinus Hypersensitivity in Patients 50 Years or over Presenting to the Accident and Emergency Department with 'Unexplained' or 'Recurrent Falls'", *Pace*, vol. 20, Mar. 1997, Part II, pp. 820–823.

Mark E. V. Petersen, et al. "Cardiac Pacing for Vasovagal Syncope: A Reasonable Therapeutic Option?", *Pace*, vol. 20, Mar. 1997, Part II, pp. 824–826.

A.B. Dey, et al., "Cardiovascular Syncope Is the Most Common Cause of Drop Attacks in the Elderly", *Pace*, vol. 20, Mar. 1997, Part II, pp. 818–819.

David G. Benditt, et al., "Clinical Experience with Thera DR Rate–Drop Response Pacing Algorithm in Carotid Sinus Syndrome and Vasovagal Syncope", *Pace*, vol. 20, Mar. 1997, Part II, pp. 832–836.

Sutton, et al., "First Steps Toward a Pacing Algorithm for Vasovagal Syncope", *Pace*, vol. 20, Mar. 1997, Part II, pp. 827–828.

*Primary Examiner*—Scott M. Getzow
*Attorney, Agent, or Firm*—Nikolai, Mersereau & Dietz, P.A.

[57] ABSTRACT

A method and apparatus for cardiac stimulation for addressing vasovagal syncope incorporates a detection algorithm in which a precipitous rate drop from a pre-existing average intrinsic heart rate value to a lower rate limit is sensed and if the patient is awake and the intrinsic rate remains below the lower rate limit for a predetermined number of beats, the patient's heart is paced at a rate that is a programmed differential above the prior average intrinsic rate for a second programmed time interval, at the conclusion of which the pacing rate is gradually decreased to the average heart rate existing prior to the sudden rate drop or to the lower rate limit.

14 Claims, 3 Drawing Sheets

CARDIAC RHYTHM MANAGEMENT DEVICE WITH DETECTION AND THERAPY FOR SUDDEN SYNCOPAL EVENTS

BACKGROUND OF THE INVENTION

I. Field of the Invention

This invention relates generally to an apparatus and method for applying pacing therapy to a patient, and more particularly for treating vasovagal syncope.

II. Discussion of the Prior Art

Sudden syncope is a condition where a patient suffers a precipitous drop in heart rate and/or blood pressure. As reported by D. A. Richardson, et al. in an article entitled "Prevalence of Cardioinhibitory Carotid Sinus Hypersensitivity in Patients 50 Years or Over Presenting to the Accident and Emergency Department with 'Unexplained' or 'Recurrent' Falls", *Pace,* Vol. 20, March 1997, Part II, pp. 820–823, a frequent, but overlooked cause of dizziness and fainting (syncope) and resulting falls is attributable to carotid sinus syndrome. Frequently, the onset of an episode is accompanied by a precipitous drop in systolic blood pressure and an attendant drop in heart rate. The condition affects many thousands of patients, and particularly, the elderly. Many such patients present at emergency rooms with a wide variety of injuries due to falling.

The Markowitz, et al. U.S. Pat. No. 5,501,701 describes the use of an implantable pacemaker in the treatment of patients who have experienced vasovagal syncope episodes. In accordance with the teachings of that patent, the detection algorithm employed requires that there be a persistent heart beat rate above a first threshold rate before a rate drop detection function can be initiated. Upon detection of a rapid rate drop from a value above the aforementioned threshold to a rate below a second, lower threshold, a persistent or stable heart rate below the lower threshold must be detected prior to initiation of therapy. The therapy consists of applying pacing pulses at a rate that is a predetermined level above the first threshold. In establishing the detection algorithm, it is up to the medical professional to program in the upper and lower thresholds and a time increment over which the drop in heart beat rate must take place. For therapy delivery, a programmed value of pacing rate above the upper threshold must be entered, along with the time value over which therapy is to take place.

Another problem with known prior art pacemakers used in treating vasovagal syncope relates to the fact that the detection and therapy algorithm is not designed to work with a rate adaptive pacemaker. If the algorithm is implemented in a rate adaptive pacemaker, it is necessary to inhibit the rate adaptive feature.

Yet another problem attended in the prior art has to do with the operability of the detection algorithm during periods of sleep. While asleep, the average heart beat rate naturally drops to a value which may be close to the lower detection threshold. Should an AV node block or other condition that may drift in and out occur, the rate may drop below the threshold causing the pacemaker to initiate therapy and suddenly begin pacing the patient's heart at a rate that is above the upper threshold. While this does not present a safety concern, it may prove bothersome in that the sudden shift in heart rate will awaken the patient and thereby disturb sleep.

SUMMARY OF THE INVENTION

In accordance with the present invention there is provided an apparatus for treating vasovagal syncope using an implantable cardiac rhythm management device of the type having a means for detecting cardiac depolarization signals and producing electrical signals related thereto. The device further includes a means for computing an average heart rate based upon the interval between the electrical signals and a means for generating cardiac stimulating pulses at timed intervals. The detection algorithm embodied in a microprocessor-based controller provides a means for sensing a drop in intrinsic heart rate from the average heart rate value (computed using a weighted auto-regressive averaging technique) to a predetermined lower rate limit value for a predetermined number of beats. Completing the device is a therapy delivery means that is responsive to the rate drop sensing means for controlling the pulse generator means so as to cause it to generate cardiac stimulating pulses at a predetermined differential rate in excess of the computed average heart rate value existing immediately prior to the sensed drop in heart rate.

When embodied in a rate adaptive pacemaker, the cardiac rhythm management device further includes a means for sensing a parameter proportional to hemodynamic demand of the patient along with provisions for the conventional lower rate limit and upper rate limit thresholds incorporated in rate adaptive pacemakers. The means, then, for treating vasovagal syncope includes a detector for sensing a drop in heart rate from the computed average heart rate existing prior to the drop down to a preprogrammed lower sensor rate limit for a predetermined number of beats. The therapy delivery means then responds to the detected rate drop causing the pulse generator to produce stimulating pulses at a predetermined differential rate in excess of the average heart rate value existing immediately prior to the drop in heart rate.

To avoid false positives, the implantable cardiac rhythm management device may also include a sensor for determining minute ventilation, allowing respiratory rate and tidal volume parameters to be derived. The therapy delivery means is not only responsive to the rate drop sensing means, but also to the respiratory parameters to inhibit application of therapy pacing pulses above the average rate when the respiratory parameters are below a prescribed threshold indicative of a patient during sleep.

Basing the administration of pacing therapy upon detection of a heart rate drop from a previous average rate offers a number of advantages not offered by prior art pacemakers having vasovagal syncope detection in therapy. By providing weighted auto-regressive averaging to establish a base line, problems due to premature atrial contractions and premature ventricular contractions are avoided. That is to say, the approach used in the preferred embodiment of the present invention provides a more robust detection of syncope even when the intrinsic rate may vary due to physiologic demand or irregular beats. It has found that a previously observed average intrinsic rate provides the best estimate of a patient's "ideal" heart rate. Using this estimate, and by adding a programmable increment to correct for vaso-dilation caused drop in blood pressure, affords an improved therapy than when a fixed absolute rate is involved.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
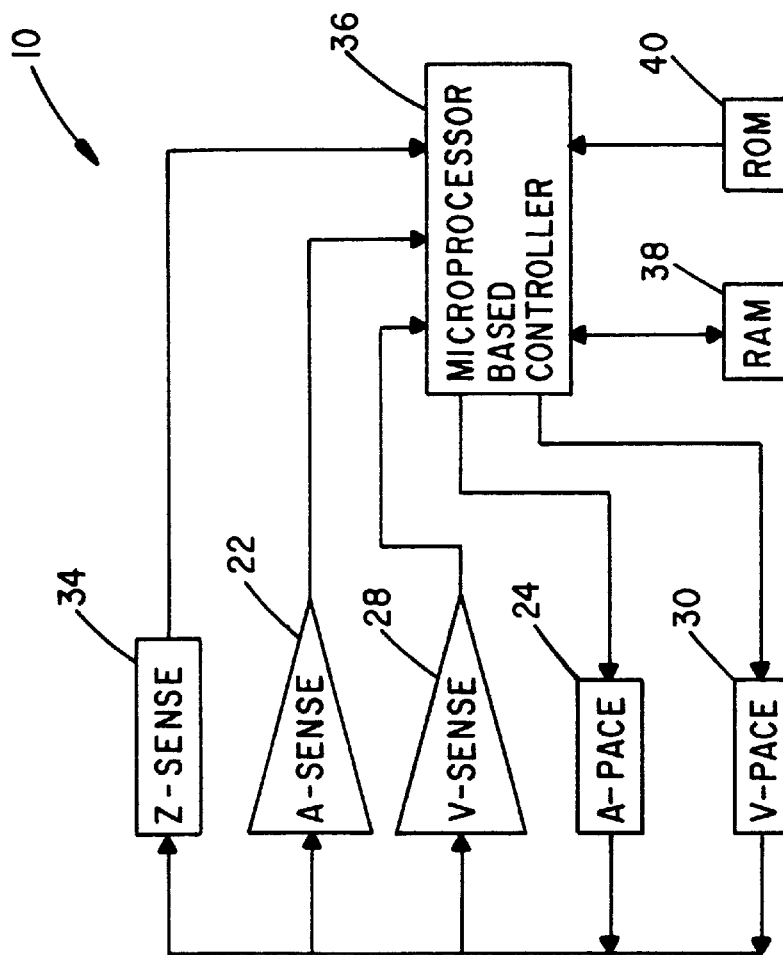
FIG. 1 is a block diagram of a cardiac rhythm management device embodying the present invention.
Figure 1:
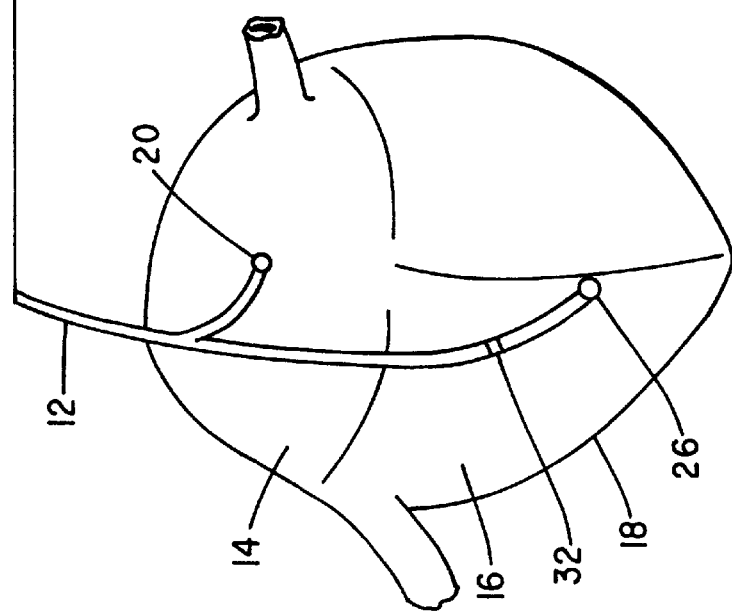

FIG. 1 illustrates by means of a block diagram, a cardiac rhythm management device 10, of a type suitable for carrying out the present invention when implanted in a patient. The cardiac rhythm management device may comprise a dual chamber pacemaker or, alternatively, a combination pacemaker defibrillator. The pacemaker 10 may be rate responsive or non-rate responsive, meaning that it may or may not have a sensor for detecting changes in hemodynamic demand and for providing a control signal related thereto to the system controller, whereby the pacing rate automatically adjusts based on such demand.

A lead 12 is shown as being disposed within the right atrial and right ventricular chambers 14 and 16, respectively, of a heart 18. The lead has at least one electrode 20 for engaging atrial tissue, whereby atrial depolarization signals can be picked up and delivered over the lead 12 to an atrial sense amplifier 22. The lead 12 also provides a way by which cardiac stimulating pulses can be delivered to atrial tissue from atrial pulse generator 24. In a similar fashion, the lead 12 includes a intracardiac distal tip electrode 26 disposed within the right ventricle 16 and it is coupled by a lead wire to the input of a ventricular sense amplifier 28. Cardiac stimulating pulses may be applied to the ventricle by a ventricular pulse generator 30 that also connects to the tip electrode 26 by a conductor in lead 12.

A further ring electrode 32 is provided on the lead 12, allowing intracardiac impedance to be sensed, via impedance sensing circuitry 34. As is known in the art, by applying a high frequency AC carrier signal between a pair of electrodes disposed in the right ventricle, such at tip electrode 26 and ring electrode 32, a current flows through the conductive blood media which is modulated by the inflow and outflow of blood from the ventricular chamber 18 occasioned by the beating action of the heart. The modulated carrier can then be demodulated and signal processed to recover a respiratory component from the impedance vs. time signal. Such an arrangement is described in detail in the Hauck et al. U.S. Pat. No. 5,318,597, the teachings of which are hereby incorporated by reference. Both minute ventilation and respiratory rate can be derived from the aforementioned respiratory component of the impedance vs. time waveform. In that minute ventilation is a parameter that varies directly with hemodynamic demand, it can function as a rate control parameter for a rate adaptive pacemaker. As those skilled in the art appreciate, other hemodynamic sensors have been devised for rate adaptive pacemakers and may be used in implementing the present invention.

The output from the atrial sense amplifier 22 and the ventricular sense amplifier 28 are applied as inputs to a microprocessor based controller 36, as is the output from the impedance sensing circuit 34. The microprocessor-based controller also has a RAM memory module 38 and a ROM module 40 operatively coupled to it, whereby a program of instructions and programmable parameters may be stored and utilized by the microprocessor-based controller 36. While a practical device will typically include additional circuitry over and above that represented in FIG. 1, e.g., a battery supply, a telemetry link and the like, the circuitry represented schematically in FIG. 1 is typical of a dual chamber implantable cardiac stimulator and is sufficient to implement and serve as a platform for the present invention.

The pacemaker 10 may operate in a variety of modes which include, DDD, DDDR, DDI, DDIR, DVI, DVIR, AAI, VVI, VVIR, VDD, etc.

Figure 2:
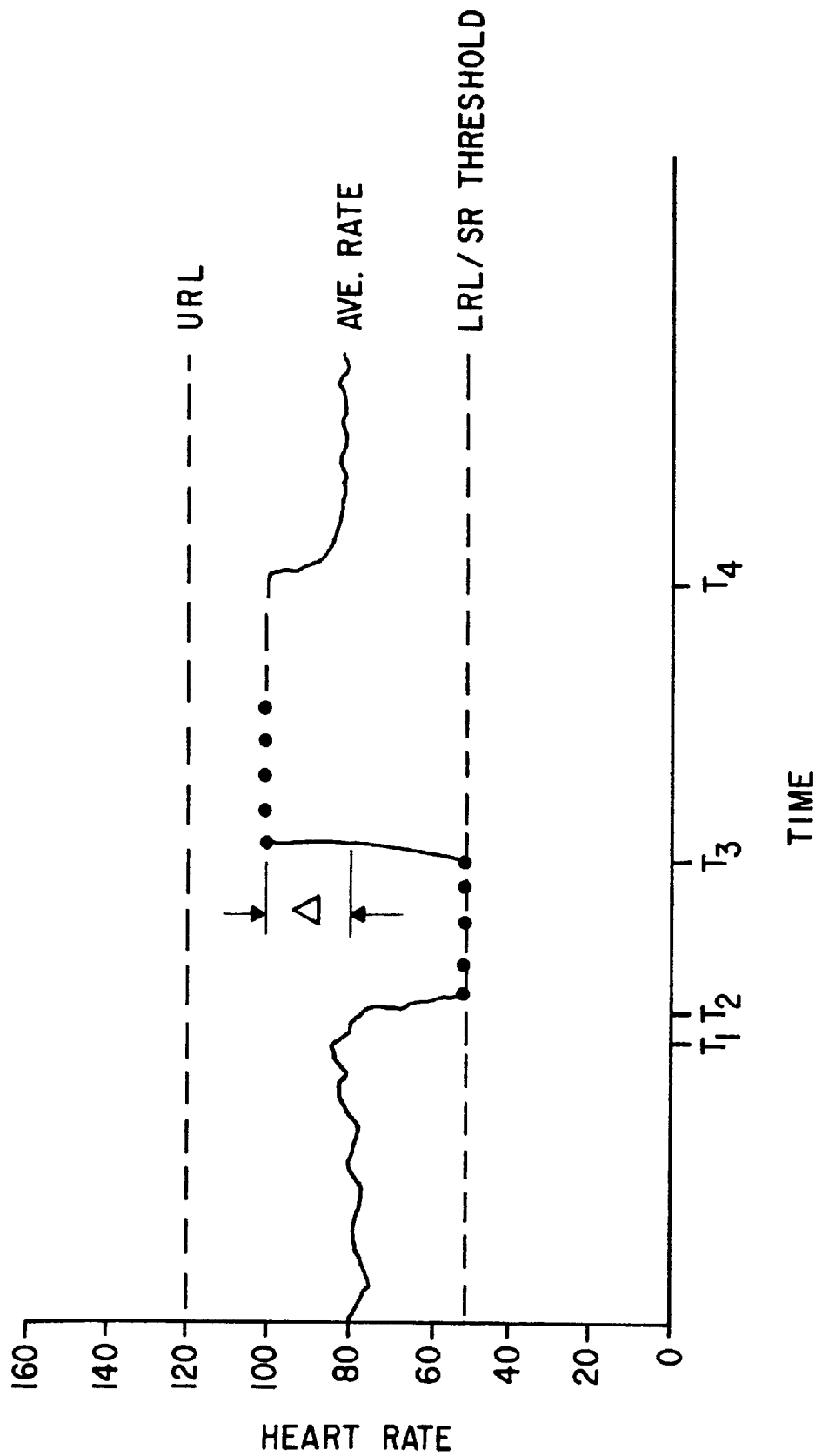
FIG. 2 is a heart rate vs. time diagram useful in explaining the operation of the present invention.

Referring to FIG. 2, there is shown a graph of heart rate vs. time that is deemed helpful in understanding the vasovagal syncope detecting and therapy algorithm involved with the implementation of the present invention. If it is assumed that the pacemaker is operating in an atrial synchronized, dual chamber mode, there will be programmed into the device a lower rate limit (LRL) at which pacing will be initiated when the patient's intrinsic rate drops to that value. As with all DDD or VDD pacemakers, an upper rate limit (URL) is also programmed in that will prevent the pacing rate from exceeding that limit even if the detected atrial depolarization rate exceeds the upper rate limit. In the graph, during the period from time 0 to time $T_1$, the patient's heart is beating at an intrinsic rate which, on the average, is about 80 bpm. During this interval, the pacemaker measures the time between either atrial depolarizations or ventricular depolarizations and computes a running average preferably using a weighted auto-regressive averaging technique. At time=$T_1$, the heart rate begins to rapidly drop and at time $T_2$ drops below the lower rate limit (LRL) which, on the graph, is set at about 50 bpm. If the pacemaker produces a predetermined number of paced beats without the intrinsic beat rising above the lower rate limit, a vasovagal syncope event is confirmed and therapy is initiated. Specifically, at time $T_3$, following, for example, 8-beats at the lower rate limit (or sensor rate in the case of a rate responsive pacer), the pacing rate is made to increase to a rate that is a predetermined differential, $\Delta$, above the previously computed running average intrinsic rate. By increasing the paced rate above the established rate immediately preceding the sudden drop, an increased blood supply is provided to the patient's brain to compensate for the depletion resulting from the sudden drop in heart rate and systolic blood pressure.

With continued reference to FIG. 2, the therapy interval from $T_3$ to $T_4$ is programmed to a value, typically, in a range of from 1 to 20 minutes. At the end of the therapy, the pacing rate is decreased over a further interval to provide graceful degradation back to the intrinsic rate or the lower rate limit.

Summarizing, a sudden syncope event is recognized when the atrial chamber has been continuously sensed for a programmable time, typically of the order of five minutes, followed by a disappearance in sensed atrial events for a programmable number of paced beats. The average intrinsic rate during this initial interval must be at least 10 bpm above the LRL prior to the drop for the drop event to be declared a syncopal event. When the sudden syncopal event is declared, the pulse generator is made to pace in the DDD mode at the greater of (1) the previous average atrial rate plus a programmed differential or (2) the sensor indicated rate if the pacer is operating in the DDDR mode. Such pacing then continues over a programmable duration, typically on the order of 1–20 minutes.

The average intrinsic rate is preferably computed using a weighted auto-regressive average. Specifically, a factor of 1/N times the current rate is summed with (N−1)/N times the preceding computed average. The computation is simplified where N is chosen to be a power of 2. This form of average obviates the need to store some number of previous rates as would be needed to calculate an arithmetic average. Additionally, this form of computation accomplishes a filtering function in time, smoothing rate excursions, yet following normal rate variations. This filtering function is useful, allowing the detection of sudden syncopal pause in heart rate, yet following normal variations.

Figure 3:
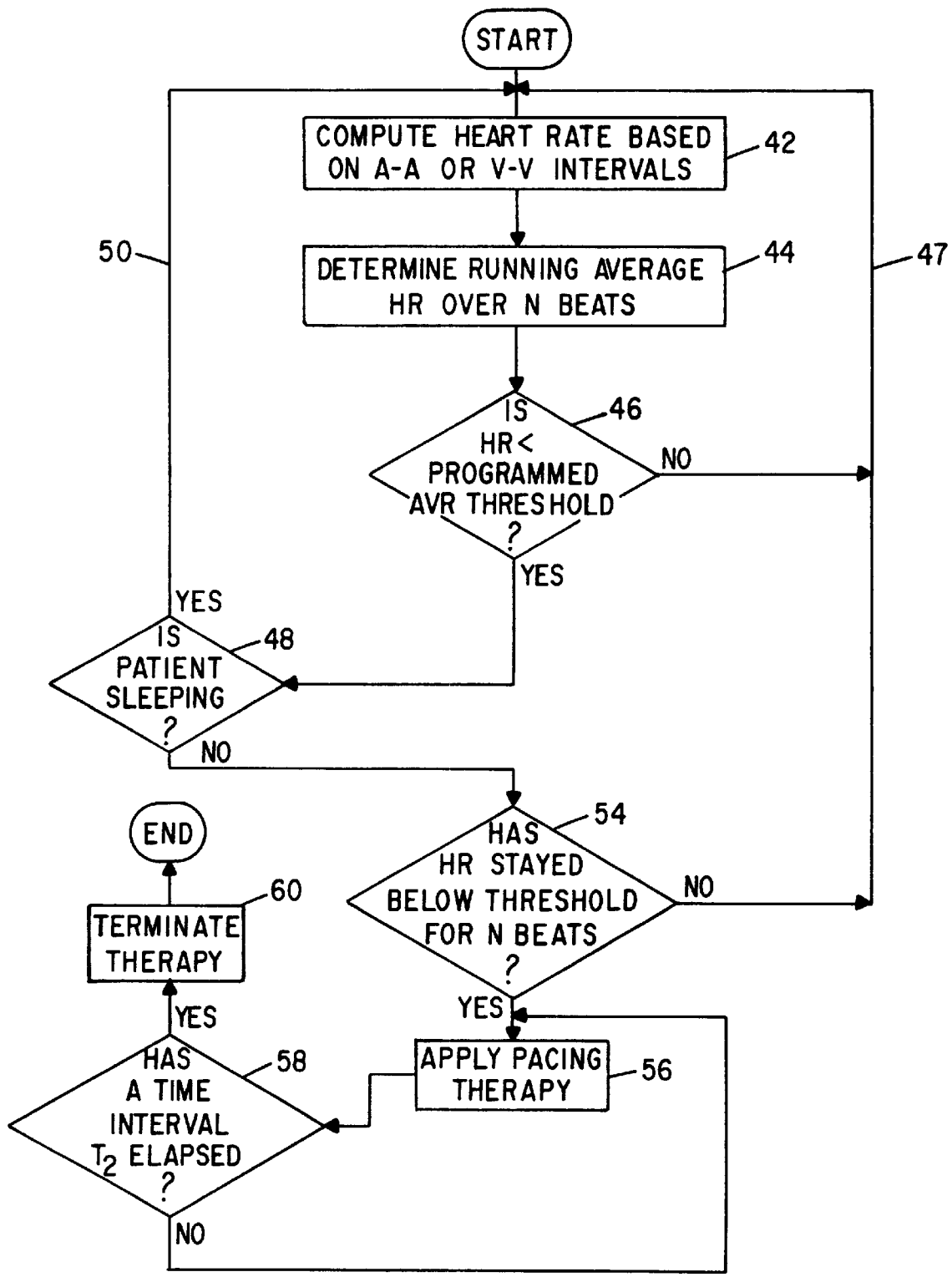
FIG. 3 is a software flow diagram of the algorithm executed by the microprocessor-based controller of FIG. 1 in implementing the present invention.

The flow diagram of FIG. 3 is representative of the algorithm executed by the microprocessor-based controller in addressing vasovagal syncope. At the start of the routine, heart rate is computed based upon A—A or V—V intervals derived from the inputs from the atrial sense amplifier 22 or the ventricular sense amplifier 28 of FIG. 1. See block 42 in FIG. 3. Next, at operation block 44, the running average heart rate over the preceding N beats is determined in the manner explained above. Next at decision block 46, a test is made to determine whether the average heart rate is less than a physician programmed (LRL) threshold and, if it is not, control passes back over line 47 to the input of operation block 42. If the average heart rate has fallen below the program threshold, a test is made at 48 to determine whether the patient is sleeping. Here, the impedance derived respiratory rate parameter obtained from processing the output from the Z-sense circuit 34 is compared to a threshold respiratory rate parameter consistent with a person who is asleep. If the test at decision block 48 reveals that the patient is sleeping, the syncope therapy is inhibited and, again, control passes back over line 50 to the input of block 42.

If the test at decision block 48 had revealed that the patient was not asleep, a further test is made at decision block 54 to determine whether the patient's heart rate has remained below the LRL or sensor rate in the case of a DDDR pacer threshold for a predetermined number, N, of beats, thus insuring that the drop was not due to an ectopic beat or other short term transient disturbance.

Thus, if the heart rate of the patient drops from its existing running average value below a predetermined threshold while the patient is awake and the heart rate has stayed below the threshold for a programmed number of beats, vasovagal syncope is confirmed and pacing therapy is applied. See block 56. As explained above, the pacing therapy involves pacing the patient's heart at a rate that is a predetermined differential above the previously computed running average rate, for example, in a range from about 5–40 beats-per-minute above the average rate. Pacing at this elevated rate continues until the test at decision block 58 reveals that a second time interval, e.g., from 1 to 20 minutes, has elapsed and at this point, the pacing rate is decreased gradually until the intrinsic heart rate value or lower rate limit is reached, at which point the syncope detection phase is re-entered at the start block in the flow chart of FIG. 3.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. In an implantable cardiac rhythm management device having means for detecting cardiac depolarization signals and for producing electrical signals related thereto, means for computing an average heart rate based upon the interval between the electrical signals, and pulse generator means for producing cardiac stimulating pulses, a means for treating vasovagal syncope comprising:
   (a) means for sensing a drop in intrinsic heart rate from the average heart rate to a predetermined lower rate threshold value for a prescribed number of beats; and
   (b) therapy delivery means responsive to the rate drop sensing means controlling the pulse generator means for generating cardiac stimulating pulses at a predetermined differential rate in excess of an average heart rate value existing immediately prior to a sensed drop in heart rate by the rate drop sensing means.

2. The implantable cardiac rhythm management device of claim 1 wherein the pulse generator means is operative to deliver a predetermined number of cardiac stimulating pulses at the lower rate threshold value prior to activation of the therapy delivery means.

3. The implantable cardiac rhythm management device of claim 2 wherein the therapy delivery means remains operative for a predetermined time interval following activation thereof.

4. The implantable cardiac rhythm management device of claim 2 wherein the device is a rate responsive pacemaker and the lower rate threshold value is a sensor determined rate.

5. The implantable cardiac rhythm management device of claim 1 wherein the means for computing an average heart rate performs a weighted auto-regressive average calculation based on a predetermined number, N, of immediately preceding intrinsic beats.

6. The implantable cardiac rhythm management device of claim 5 wherein the weighted auto-regressive average calculation forms the sum of 1/N times a current rate and (N–1)/N times a preceding average rate on a beat-by-beat basis.

7. In an implantable cardiac rhythm management device having means for detecting cardiac depolarization signals and producing electrical signals related thereto, means for determining minute ventilation of a patient in whom the implantable cardiac rhythm management device is implanted, means for computing an average heart rate based upon the interval between the electrical signals, and pulse generating means for producing cardiac stimulating pulses, a means for treating vasovagal syncope comprising:
   (a) means for sensing a drop in intrinsic heart rate from the average heart rate to a predetermined lower rate threshold value;
   (b) means responsive to the means for determining minute ventilation for deriving a respiratory rate parameter; and
   (c) therapy delivery means responsive to the rate drop sensing means and the respiratory rate parameter for controlling the pulse generator means for generating cardiac stimulating pulses at a predetermined differential rate in excess of an average heart rate value existing immediately prior to a sensed drop in heart rate by the rate drop sensing means only when the respiratory rate parameter is above a prescribed threshold.

8. The implantable cardiac rhythm management device of claim 7 wherein the pulse generator means is operative to delivery a predetermined number of cardiac stimulating pulses at the predetermined lower rate threshold prior to activation of the therapy delivery means.

9. The implantable cardiac rhythm management device of claim 8 wherein the therapy delivery means remains operative for a predetermined time interval following activation thereof.

10. The implantable cardiac rhythm management device of claim 7 wherein the means for computing an average heart rate performs a weighted auto-regressive average calculation based on a predetermined number, N, of immediately preceding intrinsic beats.

11. The implantable cardiac rhythm management device of claim 10 wherein the average calculation forms a sum of 1/N times a current rate and (N−1)/N times a preceding average rate on a beat-by-beat basis.

12. The implantable cardiac rhythm management device of claim 7 wherein the device is a rate responsive pacemaker and the predetermined lower rate threshold value is a sensor indicated rate.

13. In an implantable cardiac rhythm management device having means for detecting cardiac depolarization signals and producing electrical signals related and producing electrical signals related thereto, means for computing an average heart rate based upon an interval between electrical signals, means for sensing a parameter proportional to hemodynamic demand of the patient, and pulse generator means controlled by the parameter sensing means for providing cardiac stimulating pulses at a rate between a lower sensor rate limit and an upper sensor rate limit, as determined by said parameter, a means for treating vasovagal syncope, comprising:

(a) means for sensing a drop in heart rate from the average heart rate to said lower sensor rate limit; and (b) therapy delivery means responsive to the rate drop sensing means for controlling the pulse generator means for generating cardiac stimulating pulses at a predetermined differential rate in excess of an average heart rate value existing immediately prior to a sensed drop in heart rate by the rate drop sensing means.

14. A method of cardiac pacing, comprising the steps of:

(a) detecting depolarizations of the heart;

(b) computing from the detected depolarizations a running average of heart beat rate;

(c) detecting a sudden drop in intrinsic heart beat rate to a predetermined lower rate threshold; and (d) delivering cardiac pacing pulses at a rate that is a predetermined rate differential above the computed average heart beat rate over a predetermined time interval.

* * * * *